US012767673B2

(12) United States Patent
Kakinuma

(10) Patent No.: US 12,767,673 B2
(45) Date of Patent: Oct. 20, 2026

(54) MONOMER COMPOSITION PRODUCTION METHOD AND MONOMER COMPOSITION

(71) Applicant: MITSUI CHEMICALS, INC., Tokyo (JP)

(72) Inventor: Naoyuki Kakinuma, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 611 days.

(21) Appl. No.: 18/260,350

(22) PCT Filed: Feb. 7, 2022

(86) PCT No.: PCT/JP2022/004742

§ 371 (c)(1),
(2) Date: Jul. 5, 2023

(87) PCT Pub. No.: WO2022/176682

PCT Pub. Date: Aug. 25, 2022

(65) Prior Publication Data

US 2024/0076304 A1 Mar. 7, 2024

(30) Foreign Application Priority Data

Feb. 17, 2021 (JP) ................................. 2021-023669

(51) Int. Cl.
*C07F 9/09* (2006.01)
*A61K 6/893* (2020.01)
*C08F 30/02* (2006.01)

(52) U.S. Cl.
CPC ................ *C07F 9/09* (2013.01); *A61K 6/893* (2020.01); *C08F 30/02* (2013.01)

(58) Field of Classification Search
CPC ........ C07C 409/02; B01J 23/002; C07F 9/09; A61K 6/893; C08F 30/02
See application file for complete search history.

(56) References Cited

U.S. PATENT DOCUMENTS

| | | | | |
|---|---|---|---|---|
| 6,121,381 | A * | 9/2000 | Deguchi et al. | C08L 75/16 525/126 |
| 2008/0306168 | A1 | 12/2008 | Craig et al. | |
| 2012/0115108 | A1 | 5/2012 | Bloemker et al. | |
| 2016/0008234 | A1 | 1/2016 | Joly et al. | |
| 2018/0044448 | A1 | 2/2018 | Moser et al. | |
| 2019/0374441 | A1 | 12/2019 | Kosugi et al. | |

FOREIGN PATENT DOCUMENTS

| | | | |
|---|---|---|---|
| CN | 101353545 | A | 1/2009 |
| JP | S62149608 | A | 7/1987 |
| JP | 2009513546 | A | 4/2009 |
| WO | 2005004819 | A1 | 1/2005 |
| WO | 2018181711 | A1 | 10/2018 |

OTHER PUBLICATIONS

Oper. Dent. 2008, 33-4, 408-412 (Moore et al.) (Year: 2008).*
ChemPhysChem 2020, 21, 2029-2046 (Year: 2020).*
J. Biomed. Mater. Res. B. Appl. Biomater. 2009, 91B, 1-4 (Polydorou et al.) (Year: 2009).*

* cited by examiner

*Primary Examiner* — Amy C Bonaparte
*Assistant Examiner* — Derek Rhoades
(74) *Attorney, Agent, or Firm* — BUCHANAN INGERSOLL & ROONEY PC

(57) ABSTRACT

A method of producing a monomer composition including a polymerizable group-containing phosphoric acid compound is provided. The method includes a step of allowing a polymerizable group-containing alcohol compound, which is a compound not containing a urethane bond, to react with phosphorus pentoxide in the presence of a urethane compound, thereby obtaining a monomer composition including a polymerizable group-containing phosphoric acid compound.

8 Claims, No Drawings

MONOMER COMPOSITION PRODUCTION METHOD AND MONOMER COMPOSITION

TECHNICAL FIELD

The present disclosure relates to a method of producing a monomer composition, and a monomer composition.

BACKGROUND ART

Polymerizable monomers, a representative example of which is an allyl compound, have hitherto been used in a variety of fields such as paints, printing plate production, optical materials, and dental materials, utilizing properties thereof such as excellent curability and transparency.

In particular, in the dental material field, polymerizable monomers are widely used in dental restoration materials such as dental composite resins used for restoration of dental caries or fracture of natural teeth, and various dental adhesives used for adhering dental composite resins to teeth, as well as in artificial teeth, denture base, and the like.

For example, Patent Document 1 discloses a composition for a crown and a bridge, which contains a diallyl phthalate prepolymer, a diallyl phthalate monomer, and a polymerization initiator.

Patent Document 1: Japanese Patent Application Laid-open (JP-A) No. S62-149608

SUMMARY OF INVENTION

Problem to be Solved by Invention

In the dental field, there are cases in which a monomer composition that includes a polymerizable monomer is required to have transparency. For example, in the case of curing a polymerizable monomer contained in a monomer composition for an application such as a dental restoration material, a low transparency of the monomer composition may make it difficult to cure the polymerizable monomer by using light.

For example, when a polymerizable group-containing phosphoric acid compound that is obtained by reaction between a polymerizable group-containing alcohol compound, such as an allyl group-containing alcohol compound, and phosphorus pentoxide is used as a polymerizable monomer, a composition that includes the polymerizable group-containing phosphoric acid compound may have a decreased transparency.

The composition according to Patent Document 1 has room for improvement with respect to transparency.

A problem to be solved by one embodiment of the present disclosure is to provide a method of producing a monomer composition that can produce a monomer composition capable of curbing a decrease in transparency, and to provide the monomer composition.

Means for Solving the Problem

Means for solving the foregoing problem include the following aspects.

<1> A method of producing a monomer composition including a polymerizable group-containing phosphoric acid compound, the method including a step of allowing a polymerizable group-containing alcohol compound, which is a compound not containing a urethane bond, to react with phosphorus pentoxide in the presence of a urethane compound, thereby obtaining a monomer composition including a polymerizable group-containing phosphoric acid compound.

<2> The method of producing a monomer composition according to <1>, wherein the urethane compound has a molecular weight per urethane bond of 700 or less.

<3> The method of producing a monomer composition according to <1> or <2>, wherein the polymerizable group-containing alcohol compound is at least one selected from the group consisting of an allyl group-containing alcohol compound and a (meth)acryloyl group-containing alcohol compound.

<4> The method of producing a monomer composition according to any one of <1> to <3>, wherein the polymerizable group-containing alcohol compound includes at least one selected from the group consisting of compounds represented by the following Formulae (B-1) to (B-7) and compounds represented by the following Formula (B-a):

(B-1)

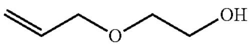

(B-2)

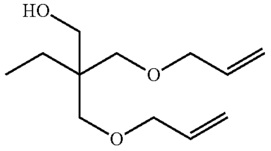

(B-3)

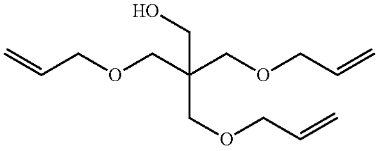

(B-4)

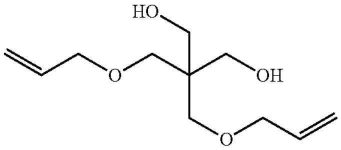

(B-5)

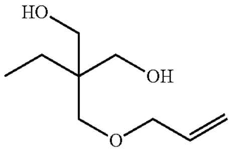

(B-6)

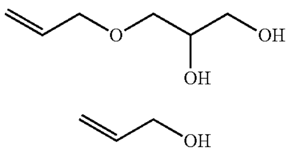

(B-7)

(B-a)

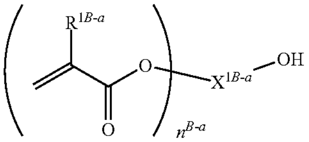

wherein, in Formula (B-a), $R^{1B-a}$ represents a hydrogen atom or a methyl group, $X^{1B-a}$ represents a $(n^{B-a}+1)$-valent organic group having 2 to 20 carbon atoms, and $n^{B-a}$ represents an integer of 1 or 2.

<5> The method of producing a monomer composition according to any one of <1> to <4>, wherein the addition mass of the urethane compound is 20% by mass or more with respect to the total addition mass of the urethane compound and the polymerizable group-containing alcohol compound.

<6> A monomer composition, including a polymerizable group-containing phosphoric acid compound and a urethane compound.

<7> The monomer composition according to <6>, wherein the monomer composition has a spectral transmittance in the range of from 400 nm to 800 nm of 40% or more under conditions of 25° C. and an optical path length of 10 mm.

<8> The monomer composition according to <6> or <7>, wherein the monomer composition is used for a dental material.

Advantageous Effect of Invention

According to the present disclosure, a method of producing a monomer composition that can produce a monomer composition capable of curbing a decrease in transparency, and the monomer composition, are provided.

MODES FOR CARRYING OUT INVENTION

In the present disclosure, any numerical range expressed using "to" means a range including numerical values described before and after "to" as a minimum value and a maximum value.

For numerical value ranges described in a stepwise manner in the present disclosure, the upper limit value or the lower limit value of one numerical value range may be replaced with the upper limit value or the lower limit value of another numerical value range in the stepwise description. The upper limit value or the lower limit value of any numerical value range described in the present disclosure may also be replaced with a value described in Examples.

In the present disclosure, the term "(meth)acryloyl" means acryloyl or methacryloyl, and the expression "(meth) acrylate" means acrylate or methacrylate.

In the present disclosure, the term "iso(thio)cyanate" means isocyanate or isothiocyanate.

In the present disclosure, the term "urethane bond" encompasses a bond formed by reaction between an isocyanate group and a hydroxy group, and a bond formed by reaction between an isothiocyanate group and a hydroxy group.

In the present disclosure, in a case in which plural substances corresponding to a component of interest are present in a composition, the amount of the component in the composition means the total amount of the plural substances present in the composition, unless otherwise specified.

<<Method of Producing Monomer Composition>>

The method of producing a monomer composition according to the present disclosure is a method of producing a monomer composition including a polymerizable group-containing phosphoric acid compound, and includes a step of allowing a polymerizable group-containing alcohol compound that is a compound not containing a urethane bond (sometimes also simply referred to as "polymerizable-group containing alcohol compound" in the present disclosure) to react with phosphorus pentoxide in the presence of a urethane compound, thereby obtaining a monomer composition including a polymerizable group-containing phosphoric acid compound (sometimes also referred to as "monomer composition production step" in the present disclosure).

The method of producing a monomer composition according to the present disclosure can curb a decrease of transparency of the resultant monomer composition, owing to the above configuration included in the method.

As described above, when phosphorus pentoxide is used in order to phosphorylate a polymerizable group-containing alcohol compound during production of a polymerizable group-containing phosphoric acid compound as a polymerizable monomer, a monomer composition that includes the resultant polymerizable group-containing phosphoric acid compound may have a reduced transparency.

In this regard, the method of producing a monomer composition according to the present disclosure includes allowing a polymerizable group-containing alcohol compound to react with phosphorus pentoxide in the presence of a urethane compound. Specifically, in the method of producing a monomer composition according to the present disclosure, the polymerizable group-containing alcohol compound and phosphorus pentoxide are not simply allowed to react with each other, but a urethane compound is made to exist during the reaction between the polymerizable group-containing alcohol compound and phosphorus pentoxide.

This configuration enables transparency reduction of the monomer composition including the resultant polymerizable group-containing phosphoric acid compound to be curbed.

The monomer composition that includes a polymerizable group-containing phosphoric acid compound and that is obtained by the method of producing a monomer composition according to the present disclosure may further include, for example, the urethane compound described above and/or a phosphoric acid group-containing urethane compound containing a urethane bond, in addition to the polymerizable group-containing phosphoric acid compound.

<Monomer Composition Production Step>

The monomer composition production step is a step of allowing a polymerizable group-containing alcohol compound to react with phosphorus pentoxide in the presence of a urethane compound, thereby obtaining a monomer composition including a polymerizable group-containing phosphoric acid compound.

That is, the monomer composition production step is a step of phosphorylating a polymerizable group-containing alcohol compound with phosphorus pentoxide in the presence of a urethane compound, to obtain a monomer composition including a polymerizable group-containing phosphoric acid compound.

In the monomer composition production step, the temperature of the reaction is not particularly limited. The temperature of the reaction is preferably from 10° C. to 50° C., more preferably from 20° C. to 40° C., and still more preferably from 20° C. to 30° C.

In order to curb a decrease in transparency, the addition amount of the urethane compound is preferably at least 20% by mass, more preferably at least 40% by mass, and still more preferably at least 60% by mass, with respect to the total addition amount of the urethane compound and the polymerizable group-containing alcohol compound.

The addition amount of the urethane compound may be at most 90% by mass, and more preferably at most 80% by mass, with respect to the total addition amount of the urethane compound and the polymerizable group-containing alcohol compound.

(Urethane Compound)

Any compound that contains a urethane bond may be used, without particular restrictions, as the urethane compound in the present disclosure.

The urethane compound in the present disclosure preferably contains one urethane bond, or preferably contains two or more urethane bonds.

The urethane compound in the present disclosure may include one allyl group, or may include two or more allyl groups.

The urethane compound in the present disclosure may include one (meth)acryloyloxy group or may include two or more (meth)acryloyloxy groups.

The urethane compound in the present disclosure may include one hydroxy group or may include two or more hydroxy groups.

In the monomer composition production step, when the urethane compound in the present disclosure contains a hydroxy group, a phosphoric acid group-containing urethane compound may be obtained by phosphorylating a hydroxy group in the urethane compound with phosphorus pentoxide.

An example of the urethane compound in the present disclosure is a urethane compound that contains a polymerizable group.

The urethane compound that contains a polymerizable group is, for example, a urethane (meth)acrylate compound (A), which contains a urethane bond and a (meth)acryloyl group but does not contain an allyl group (hereinafter sometimes also referred to as a "urethane (meth)acrylate compound (A)") or a urethane allyl compound (B), which contains a urethane bond and an allyloxy group (hereinafter sometimes also referred to as a "urethane allyl compound (B)").

Examples of the urethane (meth)acrylate compound (A) include a reaction product (a-1), which is a reaction product of an alcohol compound that contains two or more hydroxy groups with an isocyanate compound that contains one or more isocyanate groups and a (meth)acryloyloxy group, and a reaction product (a-2), which is a reaction product of an isocyanate compound that contains two or more isocyanate groups with an alcohol compound that contains one or more hydroxy groups and a (meth)acryloyloxy group.

The urethane (meth)acrylate compound (A) may include a hydroxy group or may include no hydroxy group.

The urethane (meth)acrylate compound (A) that contains a hydroxy group may be a reaction product that (i) is a reaction product (a-3), which is a reaction product of an isocyanate compound that contains one isocyanate group and a (meth)acryloyloxy group with an alcohol compound that contains three or more hydroxy groups, and (ii) contains a hydroxy group (i.e., a reaction product in which an unreacted hydroxy group among hydroxy groups contained in the alcohol compound remains), and the reaction product preferably contains one hydroxy group.

The isocyanate compound that contains two or more isocyanate groups for the reaction product (a-2) is not particularly limited, and preferably includes at least one selected from the group consisting of m-xylylene diisocyanate, 1,3-tetramethylxylylene diisocyanate, a mixture of 2,2,4-trimethylhexamethylene diisocyanate and 2,4,4-trimethylhexamethylene diisocyanate, a mixture of 2,5-bis(isocyanatomethyl)bicyclo[2.2.1]heptane and 2,6-bis(isocyanatomethyl)bicyclo[2.2.1]heptane, and isophorone diisocyanate.

The alcohol that contains one or more hydroxy groups and a (meth)acryloyloxy group for the reaction product (a-2) is not particularly limited, and preferably includes at least one selected from the group consisting of 2-hydroxyethyl (meth)acrylate, 2-hydroxypropyl (meth)acrylate, 2-hydroxybutyl (meth)acrylate, 4-hydroxybutyl (meth)acrylate, 2-hydroxy-3-phenoxypropyl (meth)acrylate, and 1,4-cyclohexanedimethanol mono(meth)acrylate.

Examples of the isocyanate compound that contains one or more isocyanate groups and a (meth)acryloyloxy group for the reaction product (a-1) include 2-methacryloyloxyethyl isocyanate (MOI).

Examples of the alcohol compound that contains two or more hydroxy groups for the reaction product (a-1) include a diol compound, which contains two hydroxy groups, and an alcohol compound that contains three or more hydroxy groups (such as tromethylolpropane or glycerin).

Examples of the isocyanate compound that contains one isocyanate group and a (meth)acryloyloxy group for the reaction product (a-3) include 2-methacryloyloxyethyl isocyanate (MOI).

Examples of the alcohol compound that contains three or more hydroxy groups for the reaction product (a-3) include trimethylolpropane and glycerin.

More specific examples of the urethane (meth)acrylate compound include 2,2,4-trimethylhexamethylene bis(2-carbamoyloxyethyl) dimethacrylate (UDMA), a reaction product of 2-methacryloyloxyethyl isocyanate (MOI) and glycerin (GLY), and a reaction product of MOI and trimethylolpropane (TMP).

Examples of the urethane allyl compound (B) include a urethane allyl compound (X), which is a urethane allyl compound that does not contain a (meth)acryloyloxy group, and a urethane allyl (meth)acrylate compound (Y), which contains a (meth)acryloyl group.

Examples of the urethane allyl compound (X) include a reaction product (X1), which is a reaction product of an isocyanate compound that contains two or more isocyanate groups with an alcohol compound that contains an allyloxy group.

The isocyanate compound that contains two or more isocyanate groups and that is used for the reaction product (X1) may be selected from the examples of the isocyanate compound that contains two or more isocyanate groups and that is used as a raw material for the urethane (meth)acrylate compound.

The alcohol compound that contains an allyloxy group for the reaction product (X1) may be selected from compounds having an allyloxy group as a polymerizable group, among the compounds exemplified in the below-described section for the polymerizable group-containing alcohol compound.

The urethane allyl (meth)acrylate compound (Y), which contains a (meth)acryloyl group is, for example, a reaction product (Y1), which is a reaction product of (i) an isocyanate compound that contains two or more isocyanate groups, (ii) an alcohol compound that contains an allyloxy group, and (iii) an alcohol compound that contains one or more hydroxy groups and a (meth)acryloyloxy group.

The isocyanate compound that contains two or more isocyanate groups for the reaction product (Y1) may be selected from the examples of the isocyanate compound that contains two or more isocyanate groups and that is used as a raw material for the urethane (meth)acrylate compound.

The alcohol compound that contains an allyloxy group and that is used for the reaction product (Y1) may be selected from compounds having an allyloxy group as a polymerizable group, among the compounds exemplified in the below-described section for the polymerizable group-containing alcohol compound.

The alcohol compound that contains one or more hydroxy groups and a (meth)acryloyloxy group and that is used for the reaction product (Y1) may be selected from the examples of the alcohol compound that contains one or more hydroxy groups and a (meth)acryloyloxy group for the reaction product (a-2).

More specific examples of the urethane allyl compound (B) include a reaction product (UDAR) of a mixture of 2,2,4-trimethylhexamethylene diisocyanate and 2,4,4-trimethylhexamethylene diisocyanate (TMHDI), with ethyleneglycol monoallyl ether (EGMA).

Examples of the urethane compound in the present disclosure include a urethane compound (C), which is a urethane compound that does not contain a polymerizable group.

The urethane compound (C), which does not contain a polymerizable group, include ethyl carbamate.

The urethane compound in the present disclosure preferably includes at least one selected from the group consisting of the urethane (meth)acrylate compound (A), which contains a urethane bond and a (meth)acryloyl group but does not contain an allyl group, and the urethane allyl compound (B), which contains a urethane bond and an allyloxy group, and the urethane compound (C), which does not contain a polymerizable group, among the compounds described above.

The urethane compound in the present disclosure has a molecular weight per urethane bond (hereinafter sometimes also referred to as "urethane bond equivalent weight") of preferably 700 or less, more preferably 500 or less, still more preferably 400 or less, and particularly preferably 300 or less, from the viewpoint of curbing a decrease in transparency.

The urethane compound in the present disclosure may have a urethane bond equivalent weight of 50 or more, or may have a urethane bond equivalent weight of 60 or more, or may have a urethane bond equivalent weight of 70 or more.

The molecular weight of the urethane compound in the present disclosure is preferably at most 2000, more preferably at most 1000, and still more preferably at most 800.

The molecular weight of the urethane compound in the present disclosure is preferably at least 70, more preferably at least 100, and still more preferably at least 150.

(Polymerizable Group-Containing Alcohol Compound)

The polymerizable group-containing alcohol compound is an alcohol compound that contains a polymerizable group.

The polymerizable group-containing alcohol compound in the present disclosure is a compound that does not contain a urethane bond.

The polymerizable group in the polymerizable group-containing alcohol compound is preferably a group that contains an ethylenic unsaturated bond, and more preferably contains at least one group selected from the group consisting of an allyl group, an allyloxy group, a (meth)acryloyl group, and (meth)acryloyloxy group.

The polymerizable group-containing alcohol compound preferably contains an allyl group or a (meth)acryloyl group as a polymerizable group, and more preferably contains an allyloxy group or a (meth)acryloyloxy group as a polymerizable group.

The polymerizable group-containing alcohol compound is preferably a compound that contains one hydroxy group and B-1 allyloxy groups connected to a B-valent connecting group. Here, B is an integer of 2 or greater, and is preferably from 2 to 4 from the viewpoint that the resultant cured product has higher fracture energy and a smaller polymerization shrinkage ratio.

The B-valent connecting group is not particularly limited, and examples thereof include a group obtainable by removing B hydrogen atoms from an alkane, a group obtainable by removing B hydrogen atoms from an arene, a group obtainable by connecting one or more groups of —C(═O)—, —$SO_2$—, —NR— (R representing a hydrogen atom or a $C_1$-$C_{10}$ alkyl group, preferably a hydrogen atom), or the like to any of the foregoing groups, and a group composed of any combination of the foregoing groups. In the group obtainable by removing B hydrogen atoms from an alkane, some of the hydrocarbon groups therein may be replaced by —C(═O)—, —$SO_2$—, —NR— (R representing a hydrogen atom or a $C_1$-$C_{10}$ alkyl group, preferably a hydrogen atom), or the like. Among them, the B-valent connecting group is preferably a group obtainable by removing B hydrogen atoms from an alkane.

The number of carbons in the alkane is preferably from 1 to 20, more preferably from 1 to 10, and still more preferably from 1 to 6. The alkane may have a substituent or may be unsubstituted. The alkane may be any of a linear alkane, a branched alkane, or a cyclic alkane. The cyclic alkane may be either monocyclic or polycyclic. Specific examples of the alkane include methane, ethane, propane, butane, 2-methylpropane, heptane, 2-methylbutane, and 2,2-dimethylpropane.

The number of carbons in the arene is preferably from 6 to 18, more preferably from 6 to 14, and still more preferably from 6 to 10. Specific examples of the arene include benzene and a condensed polycyclic aromatic compound obtainable by condensation of two or more aromatic rings.

The polymerizable group-containing alcohol compound is not particularly limited, and examples thereof include ethyleneglycol monoallyl ether, trimethylolpropane diallyl ether, pentaerythritol triallyl ether, and glycerin monoallyl ether.

The polymerizable group-containing alcohol compound may be used singly, or in combination of two or more thereof.

The polymerizable group-containing alcohol compound is preferably at least one selected from the group consisting of an allyl group-containing alcohol compound and a (meth) acryloyl group-containing alcohol compound.

The polymerizable group-containing alcohol compound preferably includes at least one selected from the group consisting of compounds represented by the following Formulae (B-1) to (B-7) and compounds represented by the following Formula (B-a).

(B-1)

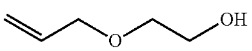

(B-2)

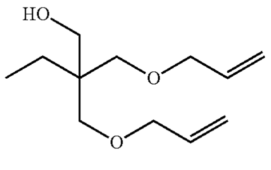

(B-3)

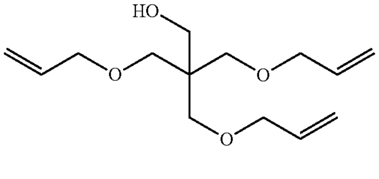

-continued (B-4)

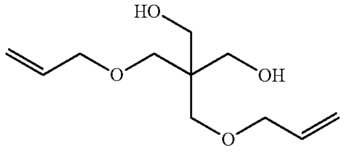

(B-5)

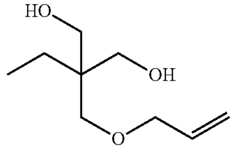

(B-6)

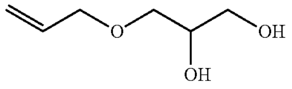

(B-7)

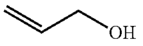

(B-a)

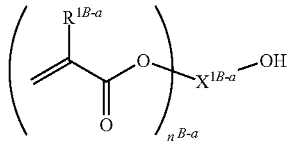

In Formula (B-a), $R^{1B\text{-}a}$ represents a hydrogen atom or a methyl group, $X^{1B\text{-}a}$ represents a $(n^{B\text{-}a}+1)$-valent organic group having 2 to 20 carbon atoms, and $n^{B\text{-}a}$ represents an integer of 1 or 2.

In Formula (B-a), $X^{1B\text{-}a}$ may be any $(n^{B\text{-}a}+1)$-valent organic group having 2 to 20 carbon atoms, without particular restrictions, and may be, for example, a $(n^{B\text{-}a}+1)$-valent organic group having 2 to 20 carbon atoms and containing a heteroatom such as an oxygen atom, a nitrogen atom, or a sulfur atom.

$X^{1B\text{-}a}$ is preferably a $(n^{B\text{-}a}+1)$-valent hydrocarbon group having 2 to 20 carbon atoms. Examples of the $(n^{B\text{-}a}+1)$-valent hydrocarbon group having 2 to 20 carbon atoms include a divalent or trivalent, linear or branched noncyclic hydrocarbon group having 2 to 20 carbon atoms, and a divalent or trivalent cyclic hydrocarbon group having 3 to 20 carbon atoms.

The number of carbons in $X^{1B\text{-}a}$ is preferably from 2 to 16, and more preferably from 2 to 14.

<<Monomer Composition>>

The monomer composition of the present disclosure includes a polymerizable group-containing phosphoric acid compound and a urethane compound. This configuration of the monomer composition of the present disclosure enables a decrease in transparency to be curbed.

The monomer composition of the present disclosure may be produced by the method of producing a monomer composition according to the present disclosure. The polymerizable group-containing phosphoric acid compound can be obtained by allowing the above-described polymerizable group-containing alcohol compound to react with the above-described phosphorus pentoxide.

From the viewpoint of curbing a decrease in transparency, the monomer composition of the present disclosure has a spectral transmittance in the range of from 400 nm to 800 nm of preferably at least 40%, more preferably at least 65%, and still more preferably at least 75%, under conditions of 25° C. and an optical path length of 10 mm.

The monomer composition of the present disclosure may have a spectral transmittance in the range of from 400 nm to 800 nm of less than 100%, or at most 95%, under conditions of 25° C. and an optical path length of 10 mm.

The content of the urethane compound in the monomer composition of the present disclosure is preferably at least 20% by mass, more preferably at least 40% by mass, and still more preferably at least 60% by mass, with respect to the total content of the polymerizable group-containing phosphoric acid compound and the urethane compound.

The content of the urethane compound in the monomer composition of the present disclosure is preferably at most 90% by mass, and more preferably at most 80% by mass, with respect to the total content of the polymerizable group-containing phosphoric acid compound and the urethane compound.

In the monomer composition of the present disclosure, the total content of the polymerizable group-containing phosphoric acid compound and the urethane compound is preferably at least 70% by mass, more preferably at least 80% by mass, and still more preferably at least 90% by mass, with respect to the total amount of the monomer composition.

The monomer composition of the present disclosure can preferably be used for dental materials. For example, in the case of using a composite resin for filling a tooth cavity caused by dental decay, the purpose can be achieved by filling, into a cavity in the mouth, the composite resin for filling a tooth cavity caused by dental decay, and thereafter photo-curing the resin, using a known photoirradiation device.

In the case of use as a composite resin for tooth crown, a desired crown material can be obtained by shaping the composition for a dental material into an appropriate shape, and then photo-curing the composition with a known photoirradiation device, and, further, performing heat treatment under predetermined conditions.

In the cases described above, the monomer composition of the present disclosure can favorably used as the composite resin for filling a tooth cavity caused by dental decay, the composite resin for tooth crown, or the like.

The monomer composition of the present disclosure can curb a decrease in transparency. Therefore, the monomer composition transmits light well, and can satisfactorily be photo-cured.

The monomer composition of the present disclosure can more preferably be used for a dental restoration material, such as a composite resin.

EXAMPLES

Examples according to the present disclosure are described below. However, the present disclosure is not limited by the following examples. The abbreviations for the compounds used in the examples according to the present disclosure are listed below.

MOI: 2-methacryloyloxyethyl isocyanate
GLY: glycerin
TMP: trimethylolpropane
TMHDI: mixture of 2,2,4-tromethylhexamethylene diisocyanate and 2,4,4-trimethylhexamethylene diisocyanate
EGMA: ethyleneglycol monoallyl ether
TMPDA: trimethylolpropane diallyl ether
PETA: pentaerythritol triallyl ether
HEMA: 2-hydroxyethyl methacrylate
HPMA: hydroxypropyl methacrylate
4HBA: 4-hydroxybutyl acrylate GDMA: glycerol dimethacrylate
DBTDL: dibutyl tin laurate
BHT: dibutylhydroxytoluene
DPPO: phosphorus pentoxide
UDMA: 2,2,4-trimethylhexamethylene bis(2-carbamoyloxyethyl) dimethacrylate (urethane bond equivalent weight: 235)
CAE: ethyl carbamate (urethane bond equivalent weight: 89)
M-GLY: reaction product of MOI and GLY (urethane bond equivalent weight: 201)
M-TMP: reaction product of MOI and TMP (urethane bond equivalent weight: 222)
UDAR: reaction product of TMHDI and EGMA (urethane bond equivalent weight: 207)

[HPLC Measurement Method]

HPLC chart spectra of (meth)acrylates obtained in the respective Examples were obtained using a HPLC instrument LC-20AT manufactured by Shimadzu Corporation. The (meth)acrylates obtained in the respective Examples were dissolved in $CH_3CN$, and then the (meth)acrylates were subjected to measurement using $CH_3CN/H_2O$=90/10 as an eluent.

[Measurement of Transmittance L]

In the Examples and Comparative Examples in the present disclosure, L was measured in the visible light region of from 400 nm to 800 nm, using a spectral color difference meter (SD-3000 manufactured by Nippon Denshoku Industries Co., Ltd.). The measurement temperature was controlled to be 25° C., and the optical path length was set to 10 mm.

[Evaluation of Transmittance]

Transmittance L in the Examples and Comparative Examples provided in the present disclosure was evaluated according to the following criteria.

A: Transmittance was 60% or more.
B: Transmittance was from 30% to less than 60%.
C: Transmittance was less than 30%.

Production Example: Hydroxy Group-Containing Urethane Methacrylate M-GLY 0.05 parts by mass of DBTDL, 0.025 parts by mass of BHT, and 11.44 parts by mass of GLY were charged into a 100 mL four-neck flask equipped with a sufficiently dried stirring blade and a thermometer. After a homogenous solution was formed by dissolution, the temperature of the solution was elevated to 80° C., and 38.56 parts by mass of MOI was dropwise added over 1 hour. Since the inner temperature increased during the dropwise addition due to reaction heat, the dropwise addition amount was controlled to maintain the temperature to be 90° C. or lower. After the entire amount of MOI was added dropwise, the reaction was allowed to proceed for 5 hours while the reaction temperature was maintained at 90° C. During the reaction, the proceeding of the reaction was monitored by HPLC analysis, and the completion of the reaction was confirmed. The product was taken out of the reactor, to obtain 50 g of M-GLY.

Production Example: Hydroxy Group-Containing Urethane Methacrylate M-TMP 0.05 parts by mass of DBTDL, 0.025 parts by mass of BHT, and 15.09 parts by mass of TMP were charged into a 100 mL four-neck flask equipped with a sufficiently dried stirring blade and a thermometer. After a homogenous solution was formed by dissolution, the temperature of the solution was elevated to 80° C., and 34.91 parts by mass of MOI was dropwise added over 1 hour. Since the inner temperature increased during the dropwise addition due to reaction heat, the dropwise addition amount was controlled to maintain the temperature to be 90° C. or lower. After the entire amount of MOI was added dropwise, the reaction was allowed to proceed for 5 hours while the reaction temperature was maintained at 90° C. During the reaction, the proceeding of the reaction was monitored by HPLC analysis, and the completion of the reaction was confirmed. The product was taken out of the reactor, to obtain 50 g of M-TMP.

Production Example: UDAR 0.05 parts by mass of DBTDL, 0.025 parts by mass of BHT, and 25.36 parts by mass of TMHDI were charged into a 100 mL four-neck flask equipped with a sufficiently dried stirring blade and a thermometer. After a homogenous solution was formed by dissolution, the temperature of the solution was elevated to 80° C., and 24.64 parts by mass of EGMA was dropwise added over 1 hour. Since the inner temperature increased during the dropwise addition due to reaction heat, the dropwise addition amount was controlled to maintain the temperature to be 90° C. or lower. After the entire amount of EGMA was added dropwise, the reaction was allowed to proceed for 5 hours while the reaction temperature was maintained at 90° C. During the reaction, the proceeding of the reaction was monitored by HPLC analysis, and the completion of the reaction was confirmed. The product was taken out of the reactor, to obtain 50 g of UDAR.

Example 1

20 parts by mass of PETA, 20 parts by mass of UDMA, and 80 mL of anhydrous methylene chloride were charged into a 100 mL four-neck flask equipped with a sufficiently dried stirring blade and a thermometer. After a homogenous solution was formed by dissolution, the solution was temperature-controlled to 20° C. Then, 6.65 g of DPPO (1.2 times the theoretically required amount) was charged in three portions. The reaction temperature was maintained at a temperature of from 20° C. to 30° C., and the reaction was allowed to proceed for 6 hours. Thereafter, 150 mL of water was slowly added into the device, to completely deactivate unreacted portion of phosphorus pentoxide while the solution temperature was maintained at room temperature. The organic layer was extracted, and volatile components were distilled away.

The product was taken out of the reactor, to obtain 35 g of a composition (1), which included a polymerizable group-containing phosphoric acid compound. The composition (1) had a transmittance at 25° C. of 82%.

Examples 2 to 19

Compositions (2) to (19), which included a polymerizable group-containing phosphoric acid compound, were obtained in the same manner as that in Example 1, except that the raw materials for the reaction were changed to combinations of compounds indicated in Table 1. The transmittance at 25° C. of the compositions (2) to (19) were as indicated in Table 1.

The compositions of Examples 3 to 6, Example 12, and Example 13 also included a phosphoric acid group-containing urethane compound.

Comparative Example 1

40 parts by mass of PETA and 80 mL of anhydrous methylene chloride were charged into a 100 mL four-neck flask equipped with a sufficiently dried stirring blade and a thermometer. After a homogenous solution was formed by dissolution, the solution was temperature-controlled to 20° C. Then, 13.29 g of DPPO (1.2 times the theoretically required amount) was charged in three portions. The reaction temperature was maintained at a temperature of from 20° C. to 30° C., and the reaction was allowed to proceed for 6 hours. Thereafter, 150 mL of water was slowly added into the device, to completely deactivate unreacted portion of phosphorus pentoxide while the solution temperature was maintained at room temperature. The organic layer was extracted, and volatile components were distilled away.

The product was taken out of the reactor, to obtain 38 g of a composition (20), which included a polymerizable group-containing phosphoric acid compound. The composition (20) had a transmittance at 25° C. of 5%.

Comparative Examples 2 to 6

Compositions (21) to (25), which included a polymerizable group-containing phosphoric acid compound, were obtained in the same manner as that in Example 1, except that the raw materials for the reaction were changed to the combinations of compounds indicated in Table 1. The transmittance of the Compositions (21) to (25) at 25° C. were as indicated in Table 1.

TABLE 1

| | | Monomer Synthesis | | | | |
|---|---|---|---|---|---|---|
| | | Hydroxy group-containing compound A | Urethane group-containing compound B | Ratio A:B | Transmittance L | Transmittance Evaluation |
| Examples | 1 | PETA | UDMA | 50:50 | 82 | A |
| | 2 | PETA | UDMA | 70:30 | 75 | A |
| | 3 | PETA | M-GLY | 50:50 | 77 | A |
| | 4 | PETA | M-GLY | 70:30 | 74 | A |
| | 5 | PETA | M-TMP | 50:50 | 78 | A |
| | 6 | PETA | M-TMP | 70:30 | 76 | A |
| | 7 | PETA | UDAR | 50:50 | 83 | A |
| | 8 | PETA | UDAR | 70:30 | 81 | A |
| | 9 | PETA | CAE | 50:50 | 74 | A |
| | 10 | PETA | CAE | 70:30 | 71 | A |
| | 11 | TMPDA | UDMA | 70:30 | 82 | A |
| | 12 | TMPDA | M-GLY | 70:30 | 81 | A |
| | 13 | TMPDA | M-TMP | 70:30 | 83 | A |
| | 14 | TMPDA | UDAR | 70:30 | 84 | A |
| | 15 | TMPDA | CAE | 70:30 | 81 | A |
| | 16 | HEMA | UDMA | 70:30 | 88 | A |
| | 17 | HPMA | UDMA | 70:30 | 89 | A |
| | 18 | 4HBA | UDMA | 70:30 | 91 | A |
| | 19 | GDMA | UDMA | 70:30 | 85 | A |
| Comparative Examples | 1 | PETA | — | 100:0 | 5 | C |
| | 2 | TMPDA | — | 100:0 | 5 | C |
| | 3 | HEMA | — | 100:0 | 45 | B |
| | 4 | HPMA | — | 100:0 | 38 | B |
| | 5 | 4HBA | — | 100:0 | 49 | B |
| | 6 | GDMA | — | 100:0 | 26 | B |

As demonstrated in Table 1, the monomer composition obtained in the Examples exhibited excellent results with respect to spectral transmittance L and evaluation thereof, wherein the method of producing a monomer composition including a step of allowing a polymerizable group-containing alcohol compound to react with phosphorus pentoxide in the presence of a urethane compound, thereby obtaining a monomer composition including a polymerizable group-containing phosphoric acid compound, is used in the Examples. Thus, a decrease in transparency was curbed in the monomer compositions according to the Examples.

In contrast, the monomer composition obtained in the Comparative Examples exhibited inferior results with respect to spectral transmittance L and evaluation thereof, wherein, in the Comparative Examples, the monomer composition including a polymerizable group-containing phosphoric acid compound was obtained by allowing a polymerizable group-containing alcohol compound to react with phosphorus pentoxide in the absence of a urethane compound. Thus, a decrease in transparency could not be curbed in the monomer compositions according to the Comparative Examples.

The disclosure of Japanese Patent Application No. 2021-023669, filed Feb. 17, 2021, is incorporate herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A method of producing a monomer composition including a polymerizable group-containing phosphoric acid compound, the method comprising:

allowing a polymerizable group-containing alcohol compound, which is a compound not containing a urethane bond, to react with phosphorus pentoxide in the presence of a urethane compound, thereby obtaining a monomer composition including a polymerizable group-containing phosphoric acid compound.

2. The method of producing a monomer composition according to claim 1, wherein the urethane compound has a molecular weight per urethane bond of 700 or less.

3. The method of producing a monomer composition according to claim 1, wherein the polymerizable group-containing alcohol compound is at least one selected from the group consisting of an allyl group-containing alcohol compound and a (meth)acryloyl group-containing alcohol compound.

4. The method of producing a monomer composition according to claim 1, wherein the polymerizable group-containing alcohol compound includes at least one selected from the group consisting of compounds represented by the following Formulae (B-1) to (B-7) and compounds represented by the following Formula (B-a):

(B-1)

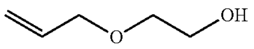

(B-2)

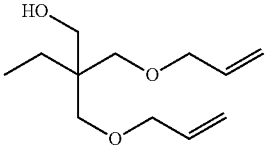

(B-3)

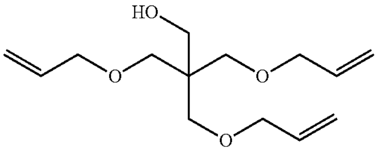

(B-4)

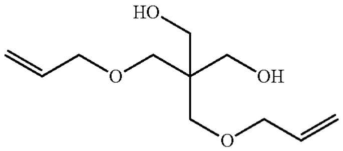

(B-5)

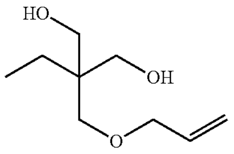

(B-6)

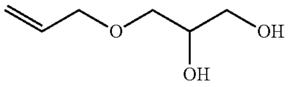

(B-7)

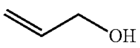

(B-a)

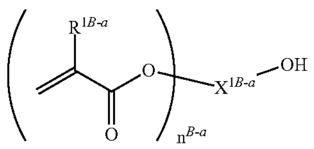

wherein, in Formula (B-a), $R^{1B\text{-}a}$ represents a hydrogen atom or a methyl group, $X^{1B\text{-}a}$ represents a $(n^{B\text{-}a}+1)$-valent organic group having 2 to 20 carbon atoms, and $n^{B\text{-}a}$ represents 1 or 2.

5. The method of producing a monomer composition according to claim 1, wherein an addition mass of the urethane compound is 20% by mass or more with respect to a total addition mass of the urethane compound and the polymerizable group-containing alcohol compound.

6. A monomer composition comprising a polymerizable group-containing phosphoric acid compound and a urethane compound, wherein the polymerizable group-containing phosphoric acid compound contains a sub-structure derived from a compound represented by any one of the following Formulae (B-1) to (B-7):

(B-1)

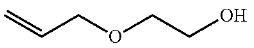

(B-2)

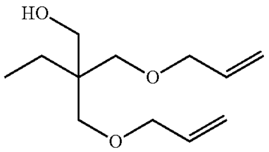

(B-3)

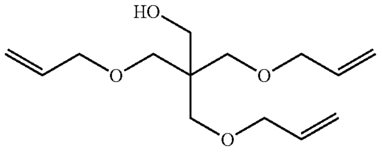

(B-4)

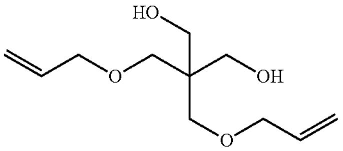

(B-5)

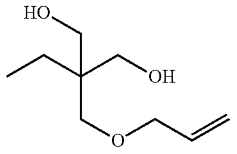

(B-6)

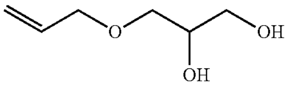

(B-7)

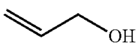

and wherein the urethane compound includes at least one selected from the group consisting of a urethane allyl compound that contains a urethane bond and an allyloxy group, and a urethane compound that does not contain a polymerizable group.

7. The monomer composition according to claim 6, wherein the monomer composition has a spectral transmittance in a range of from 400 nm to 800 nm of 40% or more under conditions of 25° C. and an optical path length of 10 mm.

8. The monomer composition according to claim 6, wherein the monomer composition is used for a dental material.

* * * * *